(12) United States Patent
Pasolini

(10) Patent No.: US 7,131,998 B2
(45) Date of Patent: Nov. 7, 2006

(54) DEVICE FOR MEASURING THE RELATIVE ANGULAR POSITION OF TWO BODIES WITH RESPECT TO A POINT, AND ARTICULAR PROSTHESIS PROVIDED THEREWITH

(75) Inventor: Fabio Pasolini, S. Martino Siccomario (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 205 days.

(21) Appl. No.: 10/825,966

(22) Filed: Apr. 15, 2004

(65) Prior Publication Data

US 2004/0267379 A1  Dec. 30, 2004

(30) Foreign Application Priority Data

Apr. 18, 2003  (IT)  ............................ TO2003A0309

(51) Int. Cl.
*A61F 2/48* (2006.01)
(52) U.S. Cl. ...................................................... 623/24
(58) Field of Classification Search ............ 623/24–25; 324/207.25, 207.23, 207.21, 252, 173–174, 324/207.22, 207.12, 207.24
See application file for complete search history.

(56) References Cited

U.S. PATENT DOCUMENTS

| 4,972,074 A | * | 11/1990 | Wright | .................. 250/227.11 |
| 5,133,216 A | * | 7/1992 | Bridges | .................. 73/862.321 |
| 5,474,088 A | * | 12/1995 | Zaharkin et al. | ............ 600/595 |
| 5,650,721 A | * | 7/1997 | van den Berg et al. | . 324/207.21 |
| 5,724,264 A | * | 3/1998 | Rosenberg et al. | ......... 702/152 |
| 5,814,093 A | * | 9/1998 | Stein | ............................ 607/49 |
| 5,933,005 A | * | 8/1999 | Pugh | ...................... 324/207.25 |
| 5,967,580 A | * | 10/1999 | Rosheim | ........................ 294/88 |
| 6,593,677 B1 | * | 7/2003 | Behin et al. | ................. 310/309 |
| 6,941,192 B1 | * | 9/2005 | Tang et al. | .................. 700/254 |

* cited by examiner

*Primary Examiner*—Alvin J. Stewart
(74) *Attorney, Agent, or Firm*—Lisa K. Jorgenson; Robert Iannucci; Seed IP Law Group PLLC

(57) ABSTRACT

A device for measuring the relative angular position of two bodies with respect to a point is provided with a first measuring element and a second measuring element, relatively movable with respect to one another and connectable to a first body and a second body, respectively; the first measuring element includes a first inclination sensor, which has a first detection axis and supplies a first inclination signal, correlated to a first angle of inclination of the first detection axis with respect to a reference axis, and the second measuring element includes a second inclination sensor, which has a second detection axis and supplies a second inclination signal, correlated to a second angle of inclination of the second detection axis with respect to the reference axis.

22 Claims, 3 Drawing Sheets

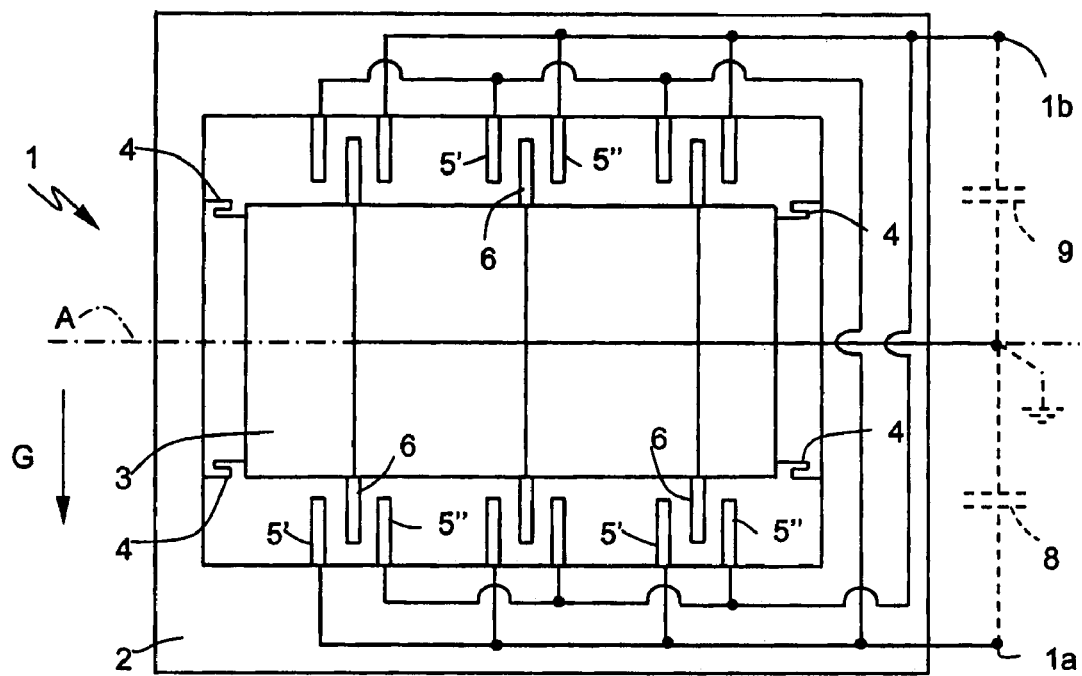
FIG. 1
*(Prior Art)*
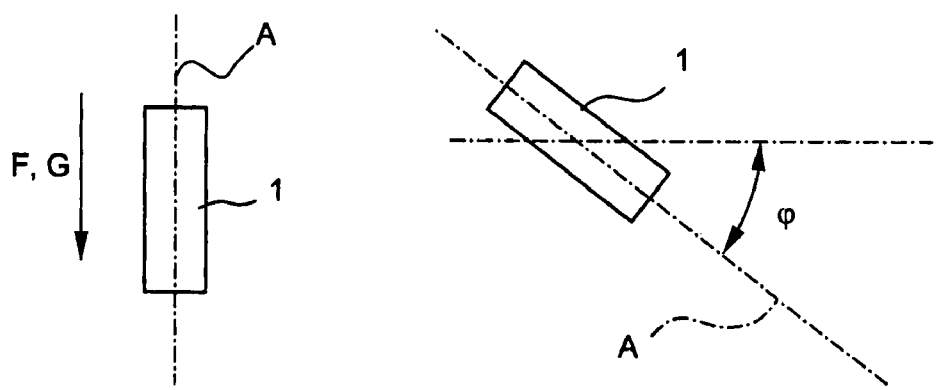
FIG. 2A
*(Prior Art)*
FIG. 2B
*(Prior Art)*

DEVICE FOR MEASURING THE RELATIVE ANGULAR POSITION OF TWO BODIES WITH RESPECT TO A POINT, AND ARTICULAR PROSTHESIS PROVIDED THEREWITH

BACKGROUND OF THE INVENTION

1. Field of the Invention

The present invention relates to a device for measuring the relative angular position of two bodies with respect to a point, and to an articular prosthesis provided therewith.

2. Description of the Related Art

As is known, active articular prostheses have been developed, which, when applied to a patient, enable a much more effective recovery of the functionality of the injured or missing limb than do traditional passive prostheses. In particular, active articular prostheses for the lower limbs (knee and ankle) tend to facilitate movement of the patient during deambulation.

Active articular prostheses comprise a pair of artificial skeletal members (for example, prostheses of tibia and femur), hinged to one another, so as to form an joint, and are provided with a control unit, an angular-position sensor, and an actuator, which is able to supply a torque between the artificial skeletal members of the joint. The angular-position sensor detects the relative angular position of the skeletal members, and the control unit, on the basis of the information supplied by the angular-position sensor, operates the actuator so as to control the movement of flexo-extension of the joint, especially during deambulation.

In known articular prostheses, angular-position sensors of a resistive type (angular potentiometers) or of an inductive type are normally used. Angular potentiometers are used for obtaining voltage dividers with variable voltage-division ratio. More precisely, an angular potentiometer is provided with a resistive element and a moving slider, in sliding electrical contact with the resistive element. The resistive element, fixed to one of the skeletal members, is thus divided into two resistive portions, and the division ratio between the two resistive portions depends upon the position of the slider, which is fixed to the other skeletal member. The information on the angular position of the skeletal members is hence supplied by the value of the voltage-division ratio. Angular sensors of an inductive type are based upon detection of the current flowing in a first winding on account of the variations in a magnetic field generated by a second winding, which is angularly movable with respect to the first winding. In particular, variations in the relative angular position of the two windings (each fixed to a respective skeletal member) modify the magnetic flux concatenated by the first winding, which is thus subject to an induced electromotive force and is traversed by a current.

Both of the types of sensors described, however, suffer from serious drawbacks that limit the performance and possibility of use thereof. In particular, angular potentiometers are readily subject to failure, have considerable encumbrance and usually require an extremely accurate assembly, in so far as even minimal misalignments are critical for their operation. In addition, angular potentiometers show problems of mechanical wear, on account of the sliding contacts. In the case of use for prostheses of the knee or ankle, these problems of wear are aggravated by the intensive use of the sensor. Angular sensors of an inductive type are more robust, have higher linearity, and do not present problems of mechanical wear. However, the encumbrance of inductive sensors is considerable, on account both of the electronic control circuits and of the shaft necessary for connection of one of the windings to the respective skeletal member. Inductive sensors are hence far from suitable for being miniaturized and integrated in a prosthesis.

BRIEF SUMMARY OF THE INVENTION

An embodiment of the present invention is to provide a device for measuring the relative position of two bodies with respect to a point, and an articular prosthesis incorporating said device, which will be free from the drawbacks described.

One embodiment of the invention is directed to a device for measuring the relative angular position of first and second bodies with respect to a point. The device includes a first measuring element and a second measuring element, relatively movable with respect to one another and connectable to the first body and, respectively, the second body. The first measuring element comprises a first inclination sensor, having a first detection axis and supplying a first inclination signal, correlated to a first angle of inclination of said first detection axis with respect to a reference axis. The second measuring element comprises a second inclination sensor, having a second detection axis and supplying a second inclination signal, correlated to a second angle of inclination of said second detection axis with respect to said reference axis.

BRIEF DESCRIPTION OF THE SEVERAL VIEWS OF THE DRAWINGS

For a better understanding of the invention, there is now described an embodiment thereof, purely by way of non-limiting example and with reference to the annexed drawings, in which:

FIG. 1 is a schematic plan view of a known inertial sensor;

FIGS. 2a and 2b are schematic illustrations of the inertial sensor of FIG. 1 in different operative configurations;

DETAILED DESCRIPTION OF THE INVENTION

Figures 3, 4:
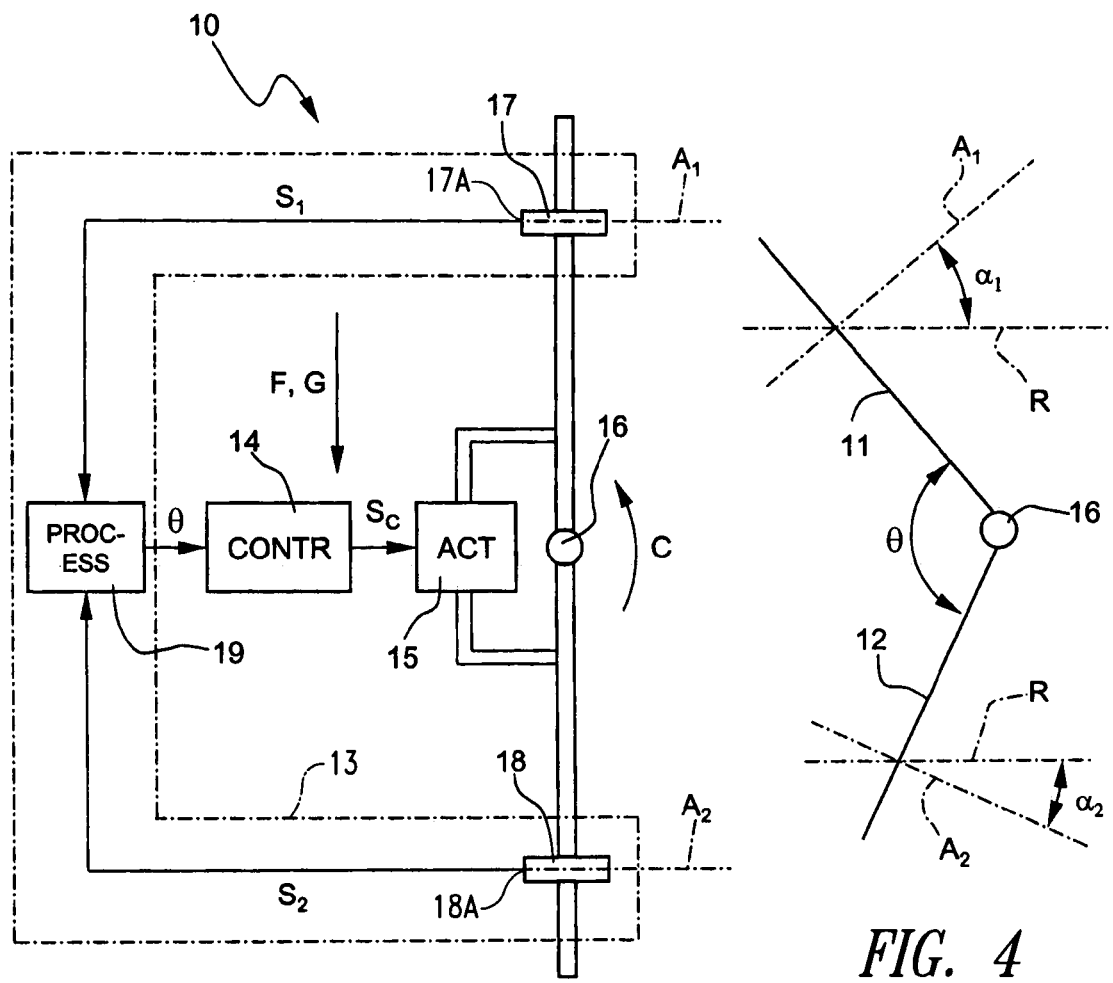
FIG. 3 is a block diagram of a prosthesis incorporating the device according to the present invention.
FIG. 4 is a schematic illustration of the prosthesis of FIG. 3 in a different operative configuration.

Illustrated in FIG. 1 is a linear inertial sensor 1 of micro-electro-mechanical (or MEMS) type, in itself known, which has a preferential detection axis A; in particular, in the configuration of FIG. 1, the detection axis A of the sensor 1 is horizontal and hence perpendicular to the direction of the acceleration of gravity G. The inertial sensor 1 comprises a stator 2 and a moving element 3, connected to one another by means of springs 4 in such a way that the moving element 3 can translate parallel to the detection axis A.

The stator 2 and the moving element 3 are provided with a plurality of first and second stator electrodes 5', 5", and, respectively, with a plurality of moving electrodes 6. Each moving electrode 6 is comprised between two respective stator electrodes 5', 5", which it is partially facing; consequently, each moving electrode 6 forms with the two mutually adjacent fixed electrodes 5', 5" a first capacitor and, respectively, a second capacitor having plane and parallel faces. In addition, all the first stator electrodes 5' are connected to a first stator terminal 1a, and all the second stator electrodes 5" are connected to a second stator terminal 1b, whereas the moving electrodes 6 are connected to ground. From the electrical standpoint, then, the inertial sensor 1 may be represented ideally by a first equivalent capacitor 8 and a second equivalent capacitor 9 (here illustrated with a dashed line); the equivalent capacitor 8 has its first terminal connected to the first stator terminal 1a, and the equivalent capacitor 9 has its first terminal connected to the second stator terminal 1b, and they each have their second terminal connected to ground. In addition, the first and second equivalent capacitors 8, 9 have variable capacitances correlated to the position of the moving element 3 with respect to the rotor 2; in particular, the capacitances of the equivalent capacitors 8, 9 at rest are equal and are unbalanced in the presence of an acceleration oriented according to the detection axis A. The capacitive unbalancing is hence indicative of the component of the resultant of the forces acting on the moving element 3 parallel to the detection axis A.

In the configuration of FIG. 1, if the acceleration of gravity G is perpendicular to the detection axis A, then the force of gravity F acting on the moving element 3 does not bring about any displacement of the moving element 3 itself. FIGS. 2a and 2b, instead, illustrate, respectively, a first configuration in which the detection axis A is vertical and hence parallel to the force of gravity F, and a second configuration in which the detection axis A is inclined at an angle $\phi$ with respect to a horizontal axis (and hence forms an angle of $90°-\phi$ with the direction of the acceleration of gravity G). In the case of FIG. 2b, the component $F_A$ of the force of gravity F along the detection axis A is:

$$F_A = F \sin \phi \tag{1}$$

Clearly, the capacitive unbalancing of the inertial sensor 1 is proportional to the component $F_A$. From equation (1), the inclination of the detection axis A with respect to the horizontal reference axis R can be readily derived:

$$\phi = \arcsin (F_A/F) \tag{2}$$

In practice, then, the inertial sensor 1 can be used as an inclinometer. With reference to FIG. 3, an articular prosthesis 10 built according to one embodiment of the present invention, in particular a knee prosthesis, comprises an artificial femur 11 and tibia 12, a device 13 for measuring the relative angular position of the femur 11 and tibia 12, a control unit 14, and an actuator 15. In FIG. 3, the femur 11 and the tibia 12 are represented schematically by rods, having respective ends connected to one another by a hinge 16.

The device 13 comprises a first inertial sensor 17 and a second inertial sensor 18, and a processing unit 19, connected to the control unit 14. The first inertial sensor 17 and the second inertial sensor 18 are identical to the inertial sensor 1 of FIG. 1, have respective preferential detection axes $A_1$, $A_2$, and are mounted on the femur 11 and, respectively, on the tibia 12. More precisely, the first and second inertial sensors 11, 12 are basically perpendicular to the axes of the femur 11 and of the tibia 12, in such a way that, when the femur 11 and the tibia 12 are aligned in the vertical direction, the detection axes $A_1$, $A_2$ of the first and second inertial sensors 17, 18 are horizontal and hence perpendicular to the direction of the acceleration of gravity G (configuration of FIG. 3). In addition, the detection axes $A_1$, $A_2$ of the first and second inertial sensors 17, 18, respectively, are basically coplanar.

Outputs 17A, 18A of the first and second inertial sensors 17, 18, respectively, are moreover connected to the processing unit 19, to supply a first inclination signal $S_1$ and a second inclination signal $S_2$, respectively. In particular, the first and second inclination signals $S_1$, $S_2$ are correlated to the capacitive unbalancing caused by the resultants of the forces acting parallel to the first detection axis $A_1$ of the first inertial sensor 11 and to the second detection axis $A_2$ of the second inertial sensor 12, respectively. On the basis of the first and second inclination signals $S_1$, $S_2$, the processing unit 19 supplies the control unit 14 with the value of angle $\theta$ comprised between the axes of the femur 11 and of the tibia 12 (see also FIG. 4). In turn, the control unit 14 has an output that is connected to the actuator 15 and supplies a control signal $S_c$ correlated to the value of the angle $\theta$. In addition, the control unit 14 and the processing unit 19 are preferably integrated in a single semiconductor body.

The actuator 15 is connected to the femur 11 and to the tibia 12 and, on the basis of the control signal $S_c$, supplies a torque C which tends to bring about a relative rotation of the femur 11 and the tibia 12 about the hinge 16. FIG. 4 illustrates a different configuration of the articular prosthesis 10 in use. In this case, the femur 11 and the tibia 12 form with respect to one another an angle $\theta$ smaller than 180°, whereas the first and second axes of detection $A_1$, $A_2$ form a first angle $\alpha_1$ and, respectively, a second angle $\alpha_2$ with respect to a horizontal reference axis R. More precisely, the angle $\theta$ is defined by the straight lines joining the hinge 16 and the first and second inertial sensors 17, 18. These straight lines coincide substantially with the longitudinal axes of the femur 11 and the tibia 12. Between the angles $\alpha_1$, $\alpha_2$, and $\theta$ there exists the following relation:

$$\theta = 180° - \alpha_1 - \alpha_2 \tag{3}$$

In particular, the angles $\alpha_1$, $\alpha_2$ are considered positive if they correspond to clockwise rotations and negative otherwise. In addition, the inclination signals $S_1$, $S_2$ are given by the following relations:

$$S_1 = S_{1MAX} \sin \alpha_1 \tag{4}$$

$$S_2 = S_{2MAX} \sin \alpha_2 \tag{5}$$

where $S_{1MAX}$ and $S_{2MAX}$ are the maximum values of the inclination signals $S_1$ and $S_2$, respectively, that can be measured when $\alpha_1 = 90°$ and when $\alpha_2 = 90°$, respectively.

The control signal $S_c$ supplied by the control unit 19 is correlated to the angle $\theta$ between the femur 11 and the tibia 12, as explained hereinafter, and, in practice, enables operation of the actuator 15 according to the movement of the patient. In particular, the actuator 15 can be used as brake when the prosthesis is loaded in the stance phase during deambulation, so as to render the deambulation itself more natural.

Figure 5:
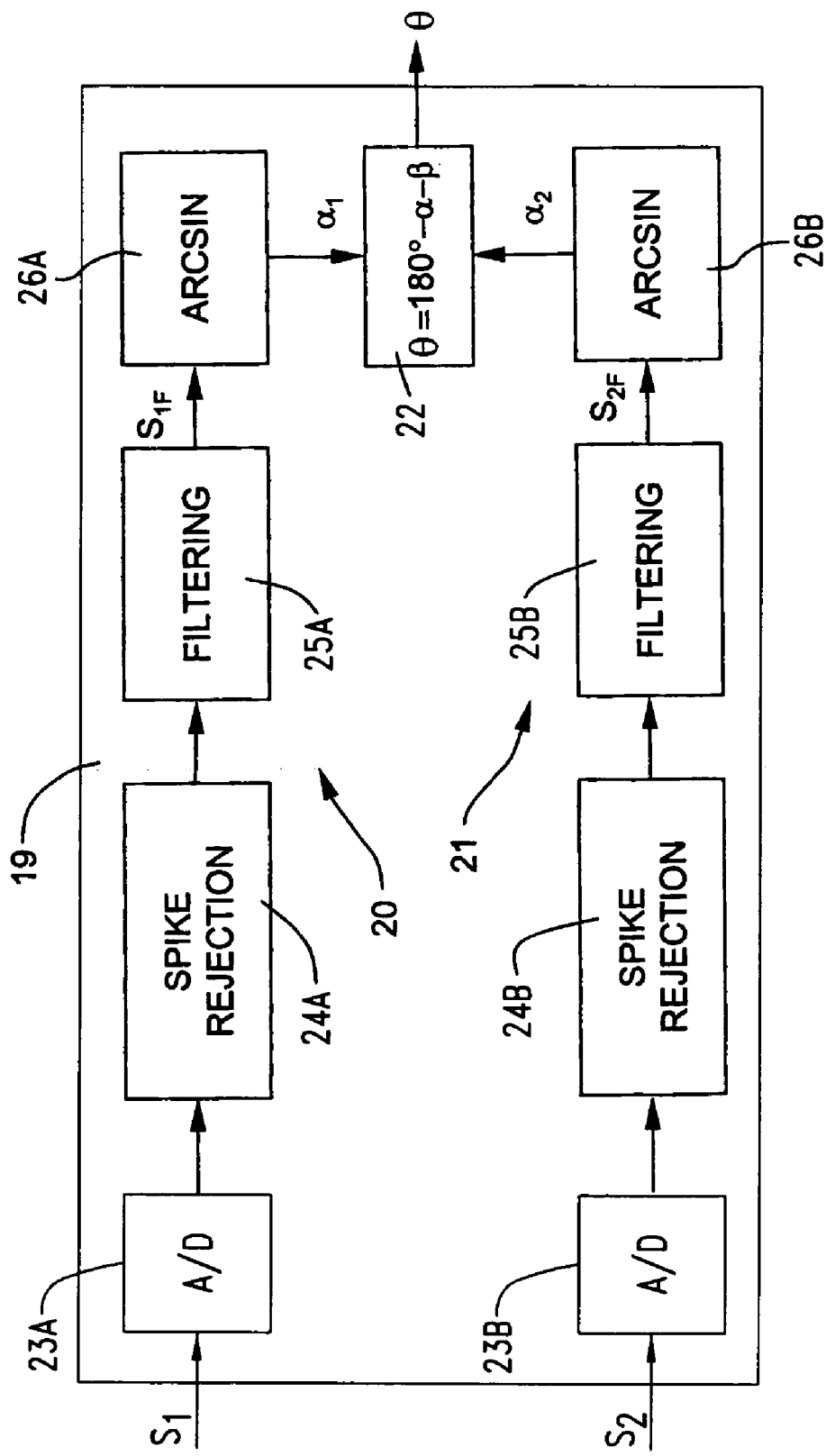
FIG. 5 is a more detailed block diagram of a part of the diagram of FIG. 3.

As is illustrated in FIG. 5, the processing unit 19 comprises a first processing line 20, which receives at input the first inclination signal $S_1$, a second processing line 21, which receives at input the second inclination signal $S_2$, and a calculation unit 22.

The first and second processing lines 20, 21 comprise respective analog-to-digital converters 23A, 23B, spike-suppression units 24A, 24B, filtering units 25A, 25B and arcsine tables 26A, 26B, connected to one another in cascaded fashion. The spike-suppression units 24A, 24B are per se known and, preferably, are of the type described in the U.S. Pat. No. 6,677,812 in the name of STMicroelectronics, the assignee of the present invention. The spike-suppression units 24A, 24B and the filtering units 25A, 25B, which are also known and are preferably of a numeric type, eliminate, from the signals $S_1$, $S_2$, the noise components due, for example, to vibrations transmitted to the inertial sensors 17, 18 in the phase of stance or of swing during deambulation. In practice, the filtering units 25A, 25B of the first and second processing lines 20, 21 supply the respective arcsine tables 26A, 26B with a first filtered inclination signal $S_{1F}$ and a second filtered inclination signal $S_{2F}$, respectively, which are correlated just to the contribution of the force of gravity F and from which it is possible to derive the values of the first and second angles $\alpha_1$, $\alpha_2$.

The arcsine tables 26A, 26B (look-up tables) of the first and second processing lines 20, 21 have outputs connected to the calculation unit 22 and supply values of the first angle $\alpha_1$, and second angles $\alpha_2$, respectively, which are selected in a known way on the basis of the values of the first and second filtered inclination signals $S_{1F}$, $S_{2F}$, respectively. The calculation unit 22 determines the value of the angle $\theta$ according to the expression (3) and supplies it to the control unit 14 (FIG. 3), which, as mentioned previously, determines the value of the control signal $S_c$ to be supplied to the actuator 15.

The advantages of the invention emerge clearly from what has been described above and are mainly due to the use of MEMS inertial sensors. These inertial sensors, in fact, are extremely compact and hence particularly suited to miniaturization. Furthermore, they do not present problems of installation on artificial skeletal members, and possible misalignments can readily be compensated by providing an offset angle during calibration. Another advantage of MEMS sensors is that the mobile parts are basically friction-free, and hence mechanical wear is minimal. In addition, power absorption of MEMS sensors is practically negligible.

In addition, the device described enables the posture of the patient to be determined, and the actuator to be deactivated or set in a stand-by condition when the patient is not deambulating. In particular, the device is able to recognize when the patient is in a sitting condition ($\alpha_1 \cong 90°$, $\alpha_2 \cong 0$) and when the patient is lying down ($\alpha_1 \cong \alpha_2 \cong -90°$). In this way, it is possible to reduce power consumption significantly.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

Finally, it is evident that modifications and variations may be made to the device described herein, without departing from the scope of the present invention. First, the device may be integrated in a prosthesis of a different joint, in particular of the ankle. Furthermore, the sensors could be differently oriented with respect to the skeletal members (for example, they could be parallel to the axes of the skeletal members) and use reference directions other than the horizontal direction for calculation of the angles of inclination $\alpha_1$, $\alpha_2$. Of course, it is possible to base the calculation of the angle $\theta$ on different angles. The arcsine tables could then be replaced with different circuits capable of carrying out the operation of extraction of the arcsine either via software or directly via hardware.

The invention claimed is:

1. A device for measuring the relative angular position of first and second bodies with respect to a point, comprising a first measuring element and a second measuring element, relatively movable with respect to one another and connectable to the first body and, respectively, the second body, wherein said first measuring element comprises a first inclination sensor, having a first detection axis and supplying a first inclination signal, correlated to a first angle of inclination of said first detection axis with respect to a reference axis, and said second measuring element comprises a second inclination sensor, having a second detection axis and supplying a second inclination signal, correlated to a second angle of inclination of said second detection axis with respect to said reference axis.

2. The device according to claim 1 wherein said first and second inclination sensors comprise a first inertial sensor and, respectively, a second inertial sensor.

3. The device according to claim 1 wherein said first and second inertial sensors are capacitive-unbalancing micro-electro-mechanical sensors.

4. The device according to the claim 3 wherein said first and second inertial sensors are linear micro-electro-mechanical sensors.

5. The device according to claim 1, further comprising a processing unit, connected to said first and second inclination sensors for receiving said first and second inclination signals, and supplying a value of an angle between said first and second bodies with respect to a pre-determined center.

6. The device according to claim 5 wherein said processing unit comprises a first processing line and a second processing line, which are connected to said first inertial sensor and to said second inertial sensor, respectively, for receiving said first inclination signal and said second inclination signal, respectively, and has outputs supplying values of said first angle of inclination and said second angle of inclination, respectively.

7. The device according to claim 6 wherein said first processing line and said second processing line comprise respective filtering circuits.

8. The device according to claim 1 wherein the first and second bodies rotate with respect to one another about a rotation axis, said first inclination sensor is connected to the first body at a first position that is spaced apart from said rotation axis, and said second inclination sensor is connected to the second body at a second position that is spaced apart from said rotation axis.

9. An articular prosthesis, comprising:
a hinge;
an artificial first skeletal member; and
an artificial second skeletal member connected to the first skeletal member by the hinge, and
a device for for determining the relative angular position of said first and second skeletal members with respect to said hinge, the device including a first measuring element and a second measuring element, relatively movable with respect to one another and connectable to the first skeletal member and, respectively, the second skeletal member, wherein said first measuring element comprises a first inclination sensor, having a first detection axis and supplying a first inclination signal, correlated to a first angle of inclination of said first detection axis with respect to a reference axis, and said second measuring element comprises a second inclination sensor, having a second detection axis and supplying a second inclination signal, correlated to a second angle of inclination of said second detection axis with respect to said reference axis.

10. The prosthesis according to claim 9 wherein said first inertial sensor is fixedly connected to said first skeletal member, and said second inertial sensor is fixedly connected to said second skeletal member.

11. The prosthesis according to claim 9 wherein said first and second axes of detection are basically coplanar.

12. The prosthesis according to claim 9, further comprising an actuator, which supplies a torque acting between said first and second skeletal members.

13. The prosthesis according to claim 12, further comprising a control unit associated to said actuator for controlling said actuator on the basis of said first and second inclination signals.

14. A device for articulating a first body with respect to a second body, comprising:
- a first measuring element and a second measuring element, relatively movable with respect to one another and connected respectively to the first body and the second body, wherein the first measuring element comprises a first inclination sensor, having a first detection axis and supplying a first inclination signal, correlated to a first angle of inclination of the first detection axis with respect to a reference axis, and the second measuring element comprises a second inclination sensor, having a second detection axis and supplying a second inclination signal, correlated to a second angle of inclination of the second detection axis with respect to the reference axis;
- a processor connected to the first and second measuring elements to receive the first and second inclination signals, the processor being structured to provide a control signal that reflects relative positions of the first and second bodies with respect to one another; and
- an actuator structurally connected to the first and second bodies and coupled to the processor, the actuator being structured to move one of the bodies with respect to the other body based on the control signal.

15. The device according to claim 14 wherein the first and second inclination sensors comprise a first inertial sensor and a second inertial sensor, respectively.

16. The device according to claim 14 wherein the first and second inertial sensors are capacitive-unbalancing micro-electro-mechanical sensors.

17. The device according to the claim 16 wherein the first and second inertial sensors are linear micro-electro-mechanical sensors.

18. The device according to claim 14, wherein the control signal supplied by the processor includes a value of an angle between the first and second bodies with respect to a pre-determined center.

19. The device according to claim 14 wherein the processor comprises a first processing line and a second processing line connected to the first inertial sensor and to the second inertial sensor, respectively, for receiving the first inclination signal and the second inclination signal, respectively, and has outputs supplying values of the first angle of inclination and the second angle of inclination, respectively.

20. The device according to claim 19 wherein the first processing line and the second processing line comprise respective filtering circuits.

21. The device according to claim 14 wherein the processor includes:
- a processing unit that receives the first and second inclination signals and outputs a value of an angle between the first and second bodies with respect to a pre-determined center; and
- a controller connected between the processing unit and the actuator, the controller being structured to produce the control signal based on the value of the angle received from the processing unit.

22. The device according to claim 14 wherein the first and second bodies rotate with respect to one another about a rotation axis, said first inclination sensor is connected to the first body at a first position that is spaced apart from said rotation axis, and said second inclination sensor is connected to the second body at a second position that is spaced apart from said rotation axis.

* * * * *